(12) United States Patent
Karp et al.

(10) Patent No.: US 11,813,075 B2
(45) Date of Patent: Nov. 14, 2023

(54) COMBINATIONAL OUTPUT SLEEP SYSTEM

(71) Applicant: HB Innovations, Inc., Los Angeles, CA (US)

(72) Inventors: Harvey Karp, Los Angeles, CA (US); Peter Fornell, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 0 days.

(21) Appl. No.: 16/752,411

(22) Filed: Jan. 24, 2020

(65) Prior Publication Data
US 2021/0228150 A1 Jul. 29, 2021

(51) Int. Cl.
*A61B 5/00* (2006.01)
*A61B 5/11* (2006.01)
*A61B 5/01* (2006.01)
*A61B 5/08* (2006.01)
*A61B 5/0205* (2006.01)

(52) U.S. Cl.
CPC ............. *A61B 5/4806* (2013.01); *A61B 5/01* (2013.01); *A61B 5/02055* (2013.01); *A61B 5/0826* (2013.01); *A61B 5/11* (2013.01); *A61B 2562/0257* (2013.01); *A61B 2562/0271* (2013.01)

(58) Field of Classification Search
CPC ...... A61B 5/4806–4818; A61B 5/0826; A61B 5/01; A61B 5/02055; A61B 5/11; A61B 2562/0257; A61B 2562/0271
See application file for complete search history.

(56) References Cited

U.S. PATENT DOCUMENTS

| | | | |
|---|---|---|---|
| 5,062,169 A | 11/1991 | Kennedy | |
| 8,562,526 B2 | 10/2013 | Heneghan | |
| 2005/0065560 A1* | 3/2005 | Lee | A61B 5/4818 607/6 |
| 2008/0052830 A1* | 3/2008 | Koughan | A47C 19/005 5/613 |
| 2010/0191136 A1* | 7/2010 | Wolford | A61B 5/00 600/534 |
| 2013/0007958 A1* | 1/2013 | Flemister | A61G 7/005 5/609 |
| 2013/0338446 A1* | 12/2013 | Van Vugt | A61B 5/4806 600/300 |
| 2014/0005502 A1* | 1/2014 | Klap | A61B 5/7282 600/301 |

(Continued)

OTHER PUBLICATIONS

International Search Report and Written Opinion of the International Searching Authority, PCT/US2021/014556, dated Apr. 14, 2021.

*Primary Examiner* — Christopher A Flory
(74) *Attorney, Agent, or Firm* — AKERMAN LLP

(57) ABSTRACT

A sleep system may include a control system for a bed device that includes platform upon which an individual may be supported. The sleep system may include multiple input sources that trigger combinational output action patterns with respect to the control system and bed device. The multiple input sources may include sensors positioned to collect input data with respect to the subject, bed device, and/or surrounding environment such as motion sensors, presence sensors, proximity sensors, sound sensors, temperature sensors, biological sensors, and/or light sensors.

16 Claims, 4 Drawing Sheets

(56) References Cited

U.S. PATENT DOCUMENTS

| | | | |
|---|---|---|---|
| 2015/0105670 A1* | 4/2015 | Bresch | A61B 5/113 600/479 |
| 2015/0335507 A1* | 11/2015 | Emmons | A61B 5/6892 5/615 |
| 2016/0015314 A1 | 1/2016 | Dusanter | |
| 2016/0058429 A1* | 3/2016 | Shinar | A61B 5/02405 600/551 |
| 2016/0174228 A1 | 6/2016 | Kubota | |
| 2016/0338871 A1 | 11/2016 | Nunn et al. | |
| 2016/0361515 A1* | 12/2016 | Jung | A61B 5/02055 |
| 2017/0135632 A1* | 5/2017 | Franceschetti | A61B 5/7271 |
| 2017/0231545 A1* | 8/2017 | Shinar | A61B 5/18 702/150 |
| 2018/0102039 A1* | 4/2018 | Furuland | A61B 5/1118 |
| 2018/0232197 A1* | 8/2018 | Ishihara | G06K 9/00543 |
| 2019/0200777 A1* | 7/2019 | Demirli | A47C 27/083 |
| 2019/0201267 A1* | 7/2019 | Demirli | A61B 5/4809 |
| 2019/0201268 A1* | 7/2019 | Sayadi | A61B 5/4809 |
| 2019/0201271 A1* | 7/2019 | Grey | A61B 5/6891 |
| 2019/0209405 A1* | 7/2019 | Sayadi | A61B 5/4809 |
| 2019/0314192 A1* | 10/2019 | Raj | A61B 5/0205 |
| 2020/0077942 A1* | 3/2020 | Youngblood | A61B 5/4884 |
| 2020/0110194 A1* | 4/2020 | Young | G01G 19/52 |
| 2020/0163627 A1* | 5/2020 | Sayadi | G01G 21/02 |
| 2020/0178887 A1* | 6/2020 | Correa Ramirez | A61B 5/4806 |
| 2020/0205580 A1* | 7/2020 | Sayadi | A47C 27/083 |
| 2020/0281521 A1* | 9/2020 | Cail | A61B 5/02055 |
| 2020/0289033 A1* | 9/2020 | Sivertsen | A61B 5/1115 |
| 2020/0337470 A1* | 10/2020 | Sayadi | A61M 21/02 |
| 2020/0405526 A1* | 12/2020 | Yu | A47G 9/1027 |
| 2021/0100366 A1* | 4/2021 | Liu | A47C 31/008 |
| 2021/0178112 A1* | 6/2021 | Ning | G16H 50/20 |
| 2022/0105308 A1* | 4/2022 | Youngblood | G16H 10/20 |
| 2022/0176065 A1* | 6/2022 | Youngblood | A61B 5/486 |
| 2022/0339398 A1* | 10/2022 | Youngblood | A61B 5/1115 |

\* cited by examiner

COMBINATIONAL OUTPUT SLEEP SYSTEM

TECHNICAL FIELD

The present disclosure relates to sleep systems including input sensors and output sources that respond to data collected by input sensors to provide combinational output patterns.

SUMMARY

A sleep system may include a control system for a bed device including platform. The control system may be separate or wholly or partially integrated with the bed device. In some embodiments, the sleep system includes the bed device. The sleep system may include multiple input sources that trigger combinational output action patterns with respect to the control system and bed device. The multiple input sources may include one or more input sensors positioned to collect input data with respect to the subject, bed device, and/or surrounding environment. Example input sensors may include motion sensors, presence sensors, proximity sensors, sound sensors, temperature sensors, biological sensors, and/or light sensors. The control system may include one or more of the input sensors and/or be configured to receive input data collected by the input sensors.

The control system may analyze the collected input data and select combinational output action patterns. Input sources analyzed by the control system to trigger combinational output action patterns may be singular or combinational. For example, brain biofeedback, breathing, pulse rate, temperature, etc. may be analyzed to understand the status of a subject, which the control system may convert into states, which may comprise sleep states. The control system may then map the states to defined output action patterns comprising motion and sound or motion, sound, and light. Other combinational output patterns may also be selected by the control system based on analysis of the collected input data such as motion, sound, lighting, temperature, or any combination thereof.

The sleep system includes one or more output devices that may be triggered by the operation of the control system to perform selected output actions specified by the control system. The control system is configured for data communication with the one or more output devices to trigger specified output actions. In some embodiments, the control system and/or bed device includes one or more of the output devices. For example, the control system and/or bed device may include one or more actuators that operably couple to the platform to execute one or more movements of the platform. The movements may include sliding back and forth (head-to-toe, side-to-side, and/or other angles) or pivoting around an axis, as examples. Sliding back-and-forth may be within a single plane or may be with respect to multiple planes (single or multiple plane arcuate movements, rocking, up and down, or the like). One or more speakers may be positioned with respect to the bed device to direct sound toward the platform or a subject located on the platform. One or more light modification devices and/or one or more temperature modification devices may also be positioned with respect to the bed device to modify and/or maintain lighting and/or temperature conditions with respect to the subject, bed device, or surrounding environment. In some embodiments, the control system may include a machine learning engine that analyzes collected input data as feedback regarding environmental factors and automatically adjusts outputs to obtain target values.

In one example, output patterns with respect to a snoring state, determined by measurements collected by sound and/or motion sensors, may be triggered. For example, the control system may identify a snoring state and specify a special combinational output pattern to address the snoring state such as triggering one or more actuators to incline a superior end of the platform corresponding the upper torso of a subject positioned on the platform relative to the inferior end of the platform.

The control system may also analyze the collected input data to detect a sleep apnea state. For example, analysis of input data collected by sound sensors, motion sensors, and/or other sensors suitable of measuring properties associated with detection of breathing, breathing patterns, and/or lack of breathing may correspond to a sleep apnea state. The control system may identify the sleep apnea state and then specify an output action pattern to minimize or otherwise address the sleep apnea state. For example, the control system trigger actuators to move the platform, such as triggering irregular movements of the platform, or other patterns.

The sleep system may include temperature modification devices. Temperature modification devices may be triggered to heat and/or cool the platform, for example.

The sleep system may include one or more variable white noise settings, which may be built-in with respect to the control system. The variable white noise settings may be accessible via interface with the control system using a user interface. The user interface may be local or remote with respect to the bed device.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

DESCRIPTION

Figure 1:
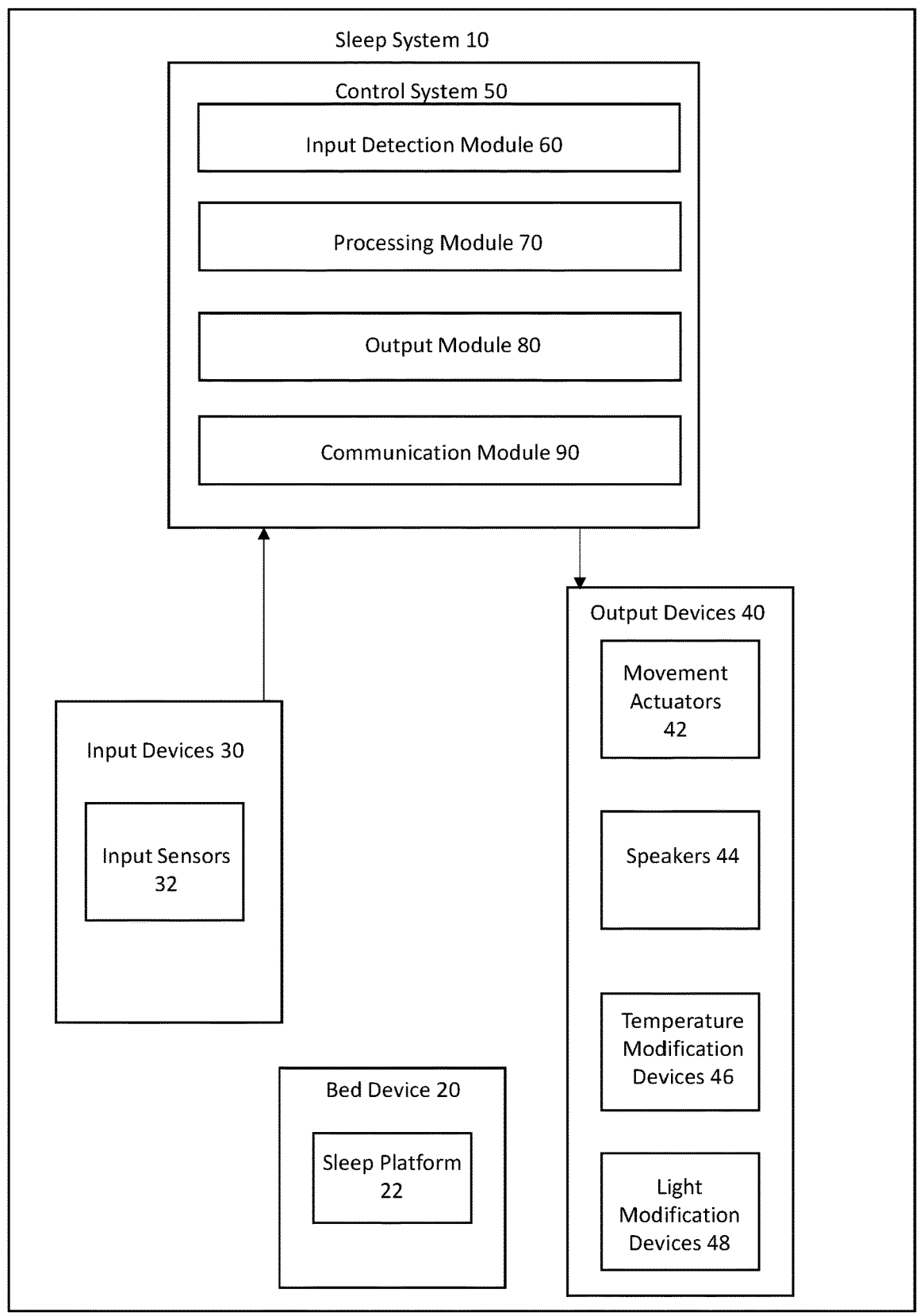
FIG. 1 illustrates a sleep system according to various embodiments described herein.

With reference to FIG. 1, a sleep system 10 may include a bed device 20 comprising a platform 22 for supporting a subject.

The sleep system 10 may include one or more input devices 30 comprising input sensors 32 operable to collect data with respect to a subject, bed device 20, and/or surrounding environment. Input sensors may include, for example, optical or imaging sensors such as cameras or light sensors, pressure sensors, temperature sensors, vibration sensors, sound sensors, biological sensors, motion sensors, and/or third party sensors. Input sensors may be integrated with the bed device, positioned around the bed device, remote with respect to the bed device, embedded in fabrics, and/or worn by a subject, e.g., on clothing, a watch, band, or headgear, as examples.

The sleep system 10 may also include one or more output devices 40 for performing output actions. Output devices 40 may be integrated with the bed device and/or be positioned with respect to the platform 22 to effectuate respective output actions with respect to the platform 10 and/or the subject. Output devices 40 may include one or more movement actuators 42 for generating movements of the platform 22, one or more speakers 44 for producing audible sound directed to the bed device or subject, one or more temperature modification devices 46 for modifying or maintaining a temperature with respect to the bed or subject, and/or one or more light modification devices 48 for generating or modifying lighting with respect to bed device 20 or subject. The bed device and/or the control system may integrate and/or associate with the input devices, output devices, or any combination thereof.

The sleep system 10 may include a control system 50 configured to control operations of the sleep system 10. The control system 50 may include an input detection module 60 configured to detect, e.g., measure, one or more properties selected from motion, sound, environmental, and/or biological properties. For example, the input detection module 60 may include one or more of the input sensors 32 or operatively associate with, e.g., receive, measurement data collected by the input sensors 32.

The control system 10 may also include a processing module 70 configured to receive and analyze the collected input data. Based at least in part on the analysis, the processing module 70 may specify an output action pattern comprising one or more output actions.

The control system 10 may also include an output module 80 to execute specified output action patterns and thereby cause performance of one or more output actions. The output module 80 may include or operatively communicate with one or more output devices 40 to execute the output action pattern. Output actions may include movements of a sleep platform 22 or portions thereof utilizing one or more movement actuators 42, sounds directed to a subject utilizing one or more speakers 44, temperature modification with respect to the sleep platform 22 utilizing one or more temperature modification devices 46, and/or lighting modification with respect to lighting directed toward the subject utilizing one or more light modification devices 48, for example. In some embodiments, output actions may include air movement modification devices such as fans and/or haptic feedback devices. The output actions may be directed to eliciting a targeted outcome with respect to a subject using the sleep system 10, which will typically be an adult human. For example, output actions may be directed to stimulating relaxation, initiation of sleep, continuation of or duration of sleep, depth of sleep, cessation of snoring, and/or breathing fluency.

The control system 10 may also include a communication module 90 configured to execute communication tasks. The communication module 90 may include one or more receivers, transmitters, or transceivers configured to facilitate wired and/or wireless communication. In some examples, the communication module 90 may provide a communication link with one or more networks, e.g., private, local area, personal area, wireless, wide area, BlueTooth, or other network. The communication module 90 may import system updates, machine learning/artificial intelligence protocols and/or data, interface with remote user interfaces, remote peripherals, which may include sensors and/or output devices, and/or user devices. The communication module 90 may link with local or remote data storage devices. The communication module 90 may interface with cloud functions and/or remote processing. The communication module 90 may transmit data to a central data analysis repository for specific and/or global analysis. As introduced above, the processing module 70 may specify an output action pattern based at least in part on the analysis of the input data. For example, the processing module 70 may determine a subject status that relates to a condition of the subject, bed, and/or environment thereof based at least in part on the analysis of the collected input data. In one embodiment, the processing module 70 may convert one or more subject statuses to one or more subject states. The processing module 70 may utilize one or more subject states to specify an output action pattern comprising one or more output actions based at least in part on the analysis. In some embodiments, specification of the output action pattern by the processing module 70 also includes consideration of one or more subject statuses or property measurements, which may or may not have been utilized when converting the one or more subject statuses to the one or more subject states.

An output action pattern may include one or more output actions. Output actions may include various parameters related to the action such as amplitude, frequency, wavelength, direction, style, type, degree, intensity, volume, cadence, varied, consistent, episodic, to name a few. Output action patterns may include combinational output actions as well as associated parameters that may be triggered by the processing module 70 in response to analysis of the collected input data. In some embodiments, the processing module 70 may include and/or generate one or more output action patterns comprising one or more output actions and associated parameters of such output actions that may be specified with respect to an identified subject state.

The control system 50 may also include an output module 80 configured to execute output action patterns specified by the processing module 70. Output action patterns specified by the processing module 70 may be directed to devices of or operable via operations of the output module 80 such as one or more sound generation devices, such as speakers 44, for generation of specified audio, movement actuators 42 for generating specified movement of a sleep platform 22 or structure on which the subject is positioned, temperature modification devices 46 for modification or maintenance of a specified ambient temperature or temperature of a sleep platform 22 or structure the subject is positioned, and/or lighting devices 48 for modification or maintenance of specified lighting with respect to a subject. For example, the output module 80 may include speakers operable to produce specified audio, lights operable to produce specified lighting, fans to control air flow, which may include movable fans and/or heaters or coolers to control temperature of the air flow generated by fans, heaters operable to increase a specified temperature with respect to a bed device or platform thereof, clothing, or environment adjacent to the bed device, coolers operable to decrease temperature with respect to a bed, clothing, or environment adjacent to a bed, actuators operable to actuate one or more portions of a bed device. Input devices 30 or sensors 32 thereof may also be used to provide feedback with respect to actions of the output module 80 as well as effect of such actions on a status of the subject.

Figure 2:
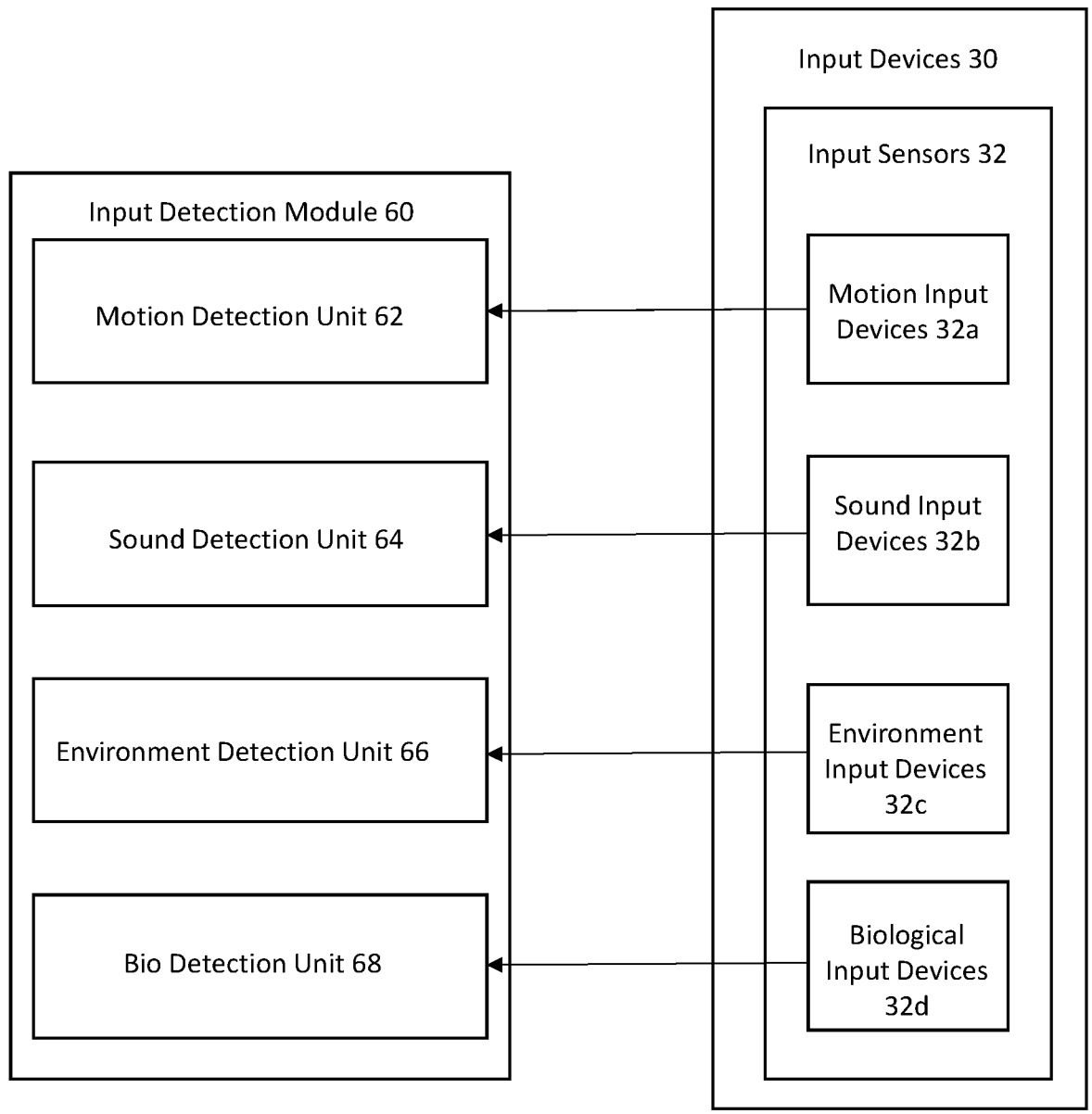
FIG. 2 illustrates an example input detection module of a control system for a bed device for controlling operations with respect to a sleep system according to various embodiments described herein.
Figure 3:
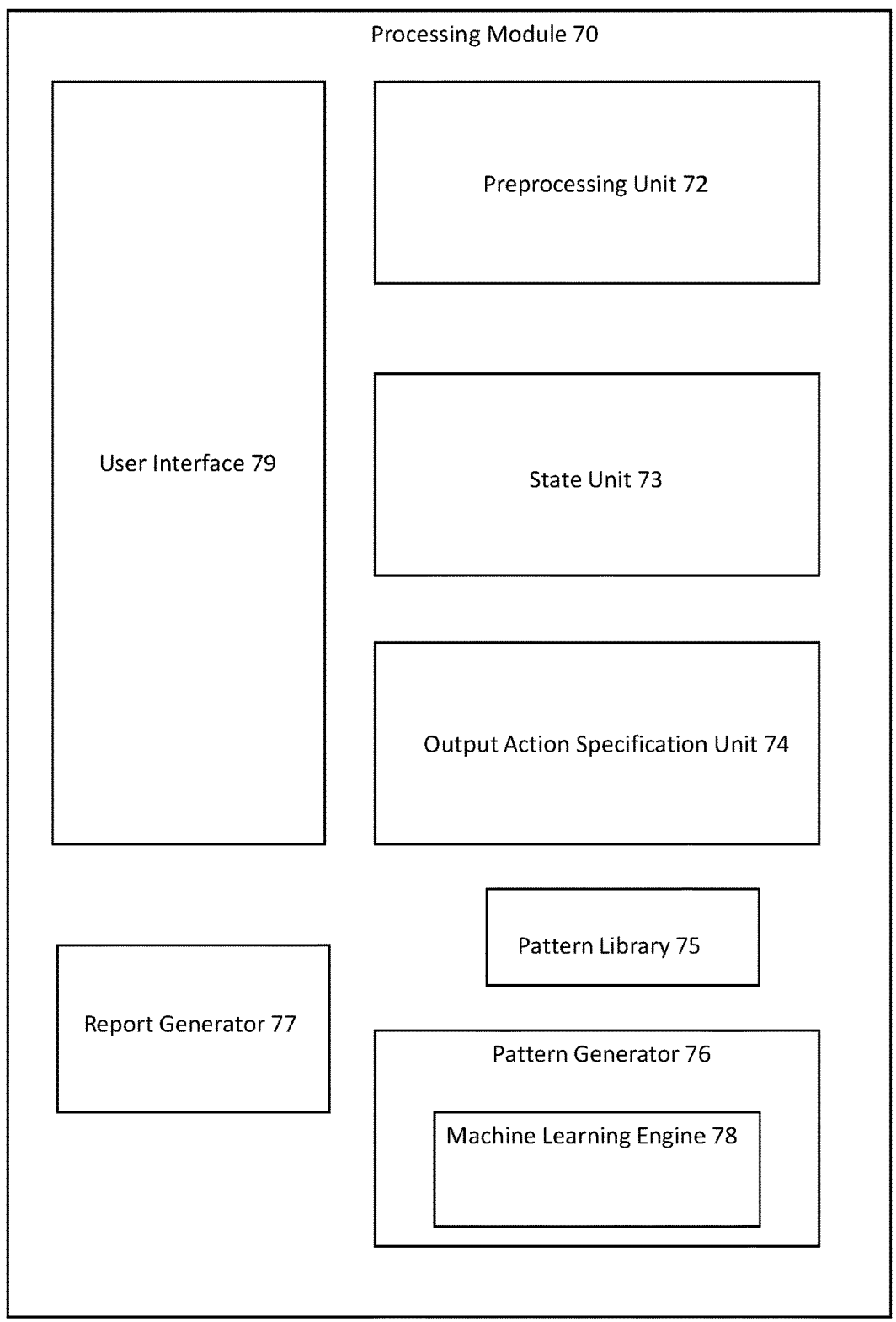
FIG. 3 illustrates an example processing module of a control system for a bed device for controlling operations with respect to a sleep system according to various embodiments described herein.
Figure 4:
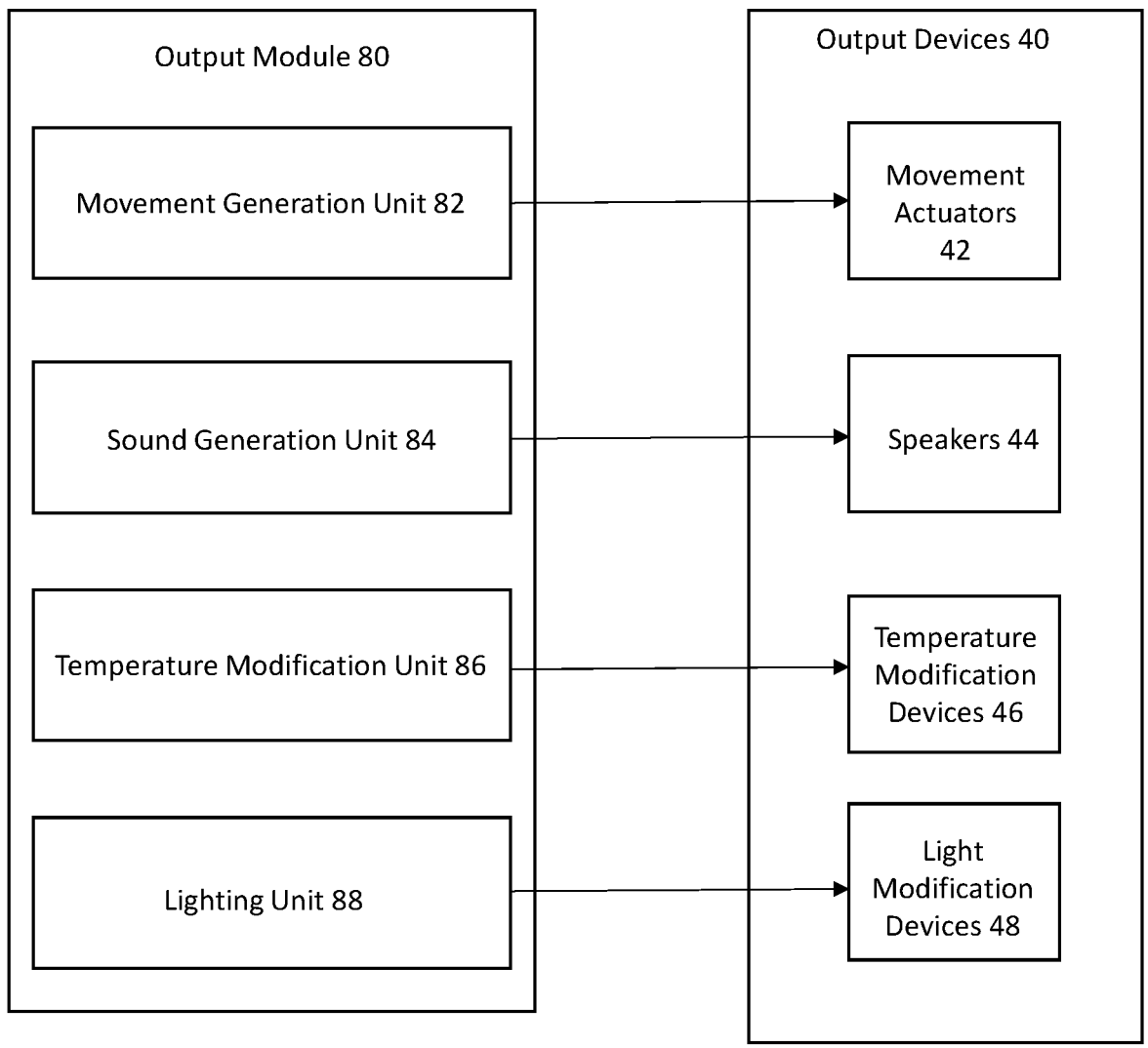
FIG. 4 illustrates an example output module of a control system for a bed device for controlling operations with respect to a sleep system according to various embodiments described herein.

FIGS. 2-4 illustrate various example modules of a control system for a bed device, which may be similar to and/or suitable for operation with the control system 10 described above with respect to FIG. 1. It is to be appreciated that the control system 10 may include various components depending on implementation needs, including various combinations of a motor, driver, sensory circuit, processor/microprocessor, databases, software, hardware, firmware, and the like operable to control the sleep system as described herein.

FIG. 2 illustrates an example input detection module 60 of the control system for a bed device. The input detection module 60 may include a motion detection unit 62 configured to detect motion, which may include proximity or presence. The detected motion may be with respect to a subject, a bed device, and/or a surrounding environment of the subject and/or bed device. The motion detection unit 62 may include and/or incorporate one or more input devices 30 including one or more motion input sensors 32a configured to detect such motion. Example motion input sensors 32a may include vibration sensors, accelerometers, gyroscopes, photo sensors, force or weight sensors, piezo sensors, optical sensors, infrared sensors, electro-optical sensor, photodiode, and/or capacitance sensors. Data obtained by the motion input sensors 32a may be transmitted to the processing module.

Motion input sensors 32a may be integrated or otherwise associated with a bed device, such as positioned or positionable in and/or around a sleep platform of the bed device. For example, a weight sensor may be integrated into a sleep platform to determine presence, weight for continuous health monitoring, and/or movement of a subject. In one example, a device or attachment containing an accelerometer or gyro may be worn by a subject. In one example, clothing, sheet, pillow, or another object associated with the subject or bed device may include markers that may be identified and/or tracked by a motion input sensor 32a to detect motion. Motion input sensors 32a may be embedded in fabric and may include flexible sensors for example. In one example, a motion input sensor 32a embedded in fabric comprises a flexible sensor. In an above or another example, a motion input sensor 32a including an imaging sensor may be positioned to capture images of a subject on the sleep platform. For example, video may be used to capture video images of the subject for image analysis to determine location, orientation, presence, proximity, breathing movement, and/or other movements or orientations of a subject. In an above or a further example, thermal or infrared imaging may be utilized to measure movements, temperature, presence, proximity, location, and/or orientation of a subject. In some embodiments, one or more motion input sensors 32a may be positioned remotely of the sleep platform and may be positioned to detect motion with respect to a subject, a bed, and/or a surrounding environment. As introduced above, detecting motion may be used to determine sleep state, such as REM phase, NREM phase, and/or N1-N3 stages of NREM. Motion detection may also be used to detect other related conditions, such as breathing, snoring, apnea, sleepwalking, insomnia, or narcolepsy, for example. Based on the information collected, other conditions and symptoms may also be detected, such as coughing, irregular movements, stirring, or twitching, as examples.

In various embodiments, the input detection module 60 may include a sound detection unit 64 configured to detect sound. The detected sound may be with respect to a subject, a bed device, and/or a surrounding environment with respect to a bed and/or subject.

The sound detection unit 64 may include or incorporate one or more input devices 30 comprising one or more sound input sensors 32b configured to detect sound. sound input sensors 32b may include, for example, microphones, pressure sensors, and/or vibration sensors. Data obtained by sound input sensors 32b may be transmitted to the processing module.

Sound input sensors 32b may be integrated or otherwise associated with a bed device, such as positioned or positionable in and/or around a sleep platform of the bed device. In one example, a microphone may be integrated or associated with clothing worn by a subject, a pillow, or sleep platform for detecting audio with respect to a subject, such as wheezing, snoring, or coughing. Sound input sensors 32b may be embedded in fabric and may include flexible sensors for example. In some embodiments, one or more sound input sensors 32b may be positioned remotely of the sleep platform and may be positioned to detect sound with respect to a subject, a bed, and/or a surrounding environment.

In some embodiments, the input detection module 60 may include an environment detection unit 66 configured to measure properties of an environment with respect to a bed device, subject, and/or surrounding environment.

Properties of the environment measured by the environment detection unit 66 may include temperature, light, atmospheric pressure, humidity. The environment detection unit 66 may include one or more input devices 30 comprising one or more environment input sensors 32c such as a thermometer, photo sensor, barometer, pressure sensor, photodetector, electro-optical sensor, contact sensor, photodiode, hygrometer, and/or other sensors suitable for measuring properties of an environment. Data obtained by environment input sensors 32c may be transmitted to the processing module.

Environment input sensors 32c may be integrated or otherwise associated with a bed device, such as positioned or positionable in and/or around a sleep platform of the bed device. For example, a temperature sensor may be integrated into a sleep platform to measure a temperature of the sleep platform. A temperature sensor may be integrated or associated with a pillow or a subject's clothing. environment input sensors 32c may be embedded in fabric and may include flexible sensors for example. In an above or another example, temperature sensors may be positioned around a sleep platform to measure ambient temperature. In one example, one or more light sensors may be integrated and/or positioned around the sleep device. In some embodiments, one or more environment input sensors 32c may be positioned remotely of the sleep platform and may be positioned to measure the environment with respect to the bed device and subject.

The input detection module 60 may include a bio detection unit 68 configured to measure biological properties of a subject.

Example biological properties measured may include heart rate, heart rhythm, breathing rate, breathing depth, body temperature, blood pressure, electrical characteristics of a subject such as of skin, brainwaves (alpha, beta, delta, theta, and/or gamma brainwaves), and/or other biological properties. The bio detection unit 68 may include and/or obtain data collected by one or more input devices 30 comprising one or more biological input sensors 32d to measure biological properties of the subject. The one or more biological input sensors 32d may include a respiration monitor, e.g., infrared finger cuff, $SpO_2$ sensor, $CO_2$ sensor, optical imaging sensor such as visual wavelength or infrared video for measurement of breathing related movements; a cardiac monitor to monitor heart beating such as a Holter monitor; a vibration sensor for detection of heart beats and/or breathing, e.g., piezo sensor; a blood pressure sensor, e.g., blood pressure cuff or implanted transducer assembly; a thermometer; a galvanic skin response (GSR) sensor; an infrared sensor; a biosensor, such as an implanted biosensor, capacitance sensor; a local or remote electroencephalography (EEG) device; and/or other suitable sensors for measuring biological properties. Data obtained by the biological sensors 32*d* may be transmitted to the processing module. In an embodiment, biological input sensors 32*d* may include an accelerometer or other vibration sensor to measure the breathing of a subject by measuring vibrations in a sleep platform or article worn by a subject.

Biological input sensors 32*d* may be integrated or otherwise associated with a bed device, such as positioned or positionable in and/or around a sleep platform of a bed device. For example, a microphone may be integrated or associated with clothing worn by a subject, a pillow, or sleep platform for detecting audio with respect to breathing and/or heart beats. Biological input sensors 32*d* may be embedded in fabric, which may include flexible sensors, for example. A subject may be fitted with a watch, strap, belt, or headgear, for example, including one or more biological input sensors 32*d*, such as one or more of a pulse monitor, GSR sensor, or body temperature thermometer. In some embodiments, one or more biological input sensors 32*d* may be positioned remotely of the sleep platform and may be positioned to obtain biological measurements remotely. For example, remote EEG and/or infrared imagining may be positioned to remotely measure brainwaves or body temperature.

FIG. 3 illustrates an example processing module 70 of the control system for a bed device. The processing module 70 may include one or more processing units, generators, engines, etc. for controlling various operations of the sleep system, which may include controlling and/or supporting one or more operations of the input detection module 60 (FIG. 2) and/or output module 80 (FIG. 4).

The processing module 70 may include various processing and/or control related components for receiving and processing inputs and generating outputs. Inputs may include data or control signals from various sensors or devices such as a user interface, microphones or sound sensors, motion sensors, presence sensors, environment sensors such as temperature sensors and/or light sensors, biological sensors, or the like.

The processing module 70 may include or be configured to access one or more databases. Databases may include, for example, a pattern library 75 and/or one or more output action databases. The processing module 70 may receive collected input data from the input detection module, specify an output action pattern based at least in part on an analysis of the collected input data, and transmit the specified output action pattern to the output module. The output action pattern transmitted may include data signals providing instructions and/or control signals for executing the specified output actions, e.g., by corresponding output module units.

In some embodiments, the processing module 70 includes a preprocessing unit 72 configured to preprocess collected input data. For example, the preprocessing unit 72 may condition collected input data, which may include signal or format conversion and/or filtering of collected input data.

In one embodiment, the preprocessing unit 72 filters collected motion data; sound data; environment data, e.g., temperature and/or light data; and/or biological data. Filtering may be used to remove signal noise, remove undesired portions of the data, and/or identify portions of the data relevant to generating an output action pattern.

Collected motion data, for example, may be filtered to identify and/or remove noise. Collected motion data may also be filtered to identify or isolate motion related to motion of a subject and/or remove motion related to the environment, such as motion of fans, caregivers, or objects. In some embodiments, movements of objects such as clothing, blankets, or pillows may be used to correspond to movement of the subject. As a further example, sound data may be filtered to remove frequencies and/or amplitudes that are not associated with a subject, such as ambient noise or sounds associated with an environment of the subject, e.g., television, radio, electronics, fans, motors, dogs, and the like. A directional filter may be used to filter sounds originating away from the sleep platform and/or subject. In some embodiments, the control module 70 does not include a preprocessing unit 72.

The processing module 70 may include a state unit 73 configured to analyze collected input data, which may or may not be preprocessed by a preprocessing unit 72, to ascertain one or more statuses of the subject. A status may include quantifications of one or more measured properties. Some measured properties may be grouped and/or determined through a combination formula. Input sources analyzed, for example, may be singular or combinational. Status may also include threshold determinants with respect to properties and/or their measured values, e.g., present. In some embodiments, certain measured properties may be excluded when one or more other measured properties are identified to be present or to be within a particular range or threshold value. In some embodiments, status may be represented in one or more scores, which may be scaled and/or normalized.

In various embodiments, collected input data may be analyzed for one or more subject statuses with respect to heartbeat, temperature, breathing, sound, and/or motion of the subject. A heart rate status, for example, may be determined from one or a combination of collected sound data, vibration data, electrocardiography, and/or imaging data, e.g., photoplethysmography. A consciousness status may be determined from brain biofeedback data, for example. In one example, alpha and/or delta brainwaves or rhythm thereof may be compared and/or measured against beta, gamma, and/or theta brainwaves. In an implementation, a breathing rate status may be obtained from analysis of motion data, vibration data, and/or sound data.

In various embodiments, the state unit 73 may determine one or more statuses with respect to movement of a subject over time, acceleration of a subject, gross motion of a subject and/or proximate environment, subject body orientation, changes in body orientation over time, sound frequency and/or amplitude with respect to the subject, sound frequency and/or amplitude with respect to an environment, ambient light intensity/amplitude and/or wavelength/frequency, heart rate, heart rhythm, breathing rate, breathing depth, breathing rhythm, respiration quality, temperature of subject, temperature of platform, blood pressure, weight of subject, brainwaves, electrical properties of the subject, or combinations thereof. In one embodiment, the state unit 73 may analyze motion data to determine a position and/or orientation of a subject. For example, infrared imaging data may be analyzed to determine a position and/or body orientation of the subject.

The state unit 73 may also convert one or more statuses to a subject state. Converting one or more statuses to a subject state may include comparing statuses to criteria for one or more subject states. For example, one or more of measured breathing status, temperature status of subject, bedding, and/or environment, duration of one or more status, hepatic status, orientation status, sound status, light status, pulse rate status, motion status, or brain biofeedback status in combination with environmental factors and time factors may be compared to defined subject states to determine if the subject is in a specified state.

A sleep state may include identification of a particular sleep state phase and/or sleep stage. Sleep may be divided into two phases non-rapid eye movement (NREM) and rapid eye movement (REM). NREM sleep has 3 stages: N1-N3. N1 stage occurs right after falling asleep and is very short, typically less than 10 minutes. During this N1 stage, individual may be easily awakened and is marked by alpha and theta waves and slowing of eye movements. N2 stage may include sudden increased brain wave frequency, sleep spindles or sigma waves, followed by a slowing or delta wave activity. N2 stage typically lasts from around 30 to 60 minutes. N3 stage is deep sleep, lasting from around 20 to 40 minutes. During N2, slower delta waves are produced and increased. Eye movement is absent and very little if any body or muscle movement occurs. REM sleep occurs about 1 to 2 hours after falling asleep. In this phase, sleep is deep and eyes may quickly jerk in different directions and brain activity increases. REM sleep may be accompanied by increases in blood pressure and heart rate. Breathing may become shallow, irregular, and increase in frequency. Brief episodes of apena may also occur. Dreaming occurs during REM sleep and the brain paralyzes muscles. Progression through the sleep phases repeats throughout the night, with the REM sleep phase typically increasing in duration from about 10 minutes to upwards of an hour. The proportion of REM sleep decreases with age, with adults spending around 20% of sleep in REM sleep while infants may spend up to 50% of sleep in REM sleep.

A snoring state may include comparing statuses such as a sound status of the subject with respect to frequency and/or amplitude corresponding to snoring and one or more statuses corresponding to a sleep state, which in some embodiments may include breathing rate status, heart rate status, and/or brain biofeedback status.

An apnea event state may include one or more statuses related to breathing, such as breathing rate, heart rate, motion data, which in some embodiments may be obtained from collected sound data, vibration data, and/or motion data, and one or more statuses corresponding to sleep, which in some embodiments may be obtained from collected motion data, heart rate data, and/or brain biofeedback data. A cold state may include one or more statuses related to breathing, such as breathing rate, depth, frequency, and/or fluency, one or more statuses related to sound such as coughing, congestion, wheezing, and/or respiratory buildup. A cold state may also include one or more statues related to motion data, e.g., detection of coughing. A fever state may include temperature status. A sleepwalking state may include motion status during sleep a state indicating the subject is not conscious, which may include brain activating, e.g., wave, status. A narcolepsy state may include detection of quick transitions between awake states and sleep states. An insomnia state may include motion status, heart rate status, breathing status, and/or duration thereof during otherwise sleep periods.

In some embodiments, the state unit 73 may be configured to define new subject states based on observation and/or learning about the subject. In this or another embodiment, the state unit 73 may be configured to define new subject states based on machine learning/artificial intelligence. The processing unit 70 may also be upgraded, e.g., communication module 90 may receive updates and/or upgrades upon request, scheduled, when available, or upon analysis of input data indicative of existence of previously unspecified subject states, to include new subject states. In one embodiment, the state unit 73 may be configured to combine two or more subject states to describe additional subject states.

One or more statuses of the surrounding environment may also be analyzed to modify a status, a state, and/or output action for specification or parameters thereof.

The processing module 70 may further include an output action specification unit 74. The output action specification unit 74 may be tasked with mapping one or more identified states to one or more output action patterns, which may include one or more output actions. In one example, an output action pattern comprises a specified output action including a movement or a series of movements of a sleep platform. In another example, an output action pattern includes one or more specified output actions such as an adjustment of a position or a single, compound, discrete, continuous, or variable movement of a sleep platform; an adjustment to ambient lighting; an adjustment to temperature of a sleep platform; and/or an initiation or modification of sound directed to a subject. In an above or another example, an output action pattern includes a sound output selected from white noise, variable white noise, noise cancellation, music, ambient sounds, nature sounds, variable frequency and/or amplitude sounds, and repetitive sounds.

The processing module 70 may also include or access a pattern library 75 that stores one or more output action patterns for selection and/or modification. The one or more output action patterns may include previously generated or preprogramed output action patterns. In one embodiment. The output action specification unit 74 includes or accesses the action pattern library 75 to specify one or more of a plurality of output action patterns for specification. Output action patterns may include defined actions or patterns of actions comprising motion, sound, temperature, and/or light patterns, for example. Some output action patterns may additionally or alternatively include air flow or haptic patterns. Output action patterns or one or more specific output actions of an output action pattern may be pre-defined or computed based on one or more statuses of the subject. In one embodiment, the pattern library includes a plurality of output action patterns that may be selected. The output action patterns may include one or more output actions wherein an output pattern generator 76 and/or machine learning engine 78 modifies the parameters of the output actions based on measured property values, states, and/or statuses of the subject. The parameters may be adjusted in real time or may be determined prior to initiation of the output action pattern or one or more output actions thereof.

Thus, using a determined state, the output action specification unit 74 may access a pattern library 75 and identify an output action pattern, which may include an output action pattern including multiple output actions or variations thereof, for specification, corresponding to the state. The specified output action pattern, which may include one or more signals for execution of one or more output actions of the output action pattern identified or computed, may be transmitted to the output module for execution as described herein.

Subject state mapping and/or identification of a corresponding output action pattern may include incorporation of parameters specific to a subject. For example, the subject may be identified by entering an identity of the subject into a user interface, biometrically or by detection of an identification card or chip worn by or in proximity to the subject. In some embodiments, the state unit 73 and/or output action specification unit 74 does not consider an identity of the subject with respect to mapping, specification of output actions, and/or generation of an output action pattern.

In one example, output patterns with respect to a snoring state, determined by measurements collected by sound and/or motion sensors, may be triggered. For example, the control system may identify a snoring state and specify a special combinational output pattern to address the snoring state such as triggering one or more actuators to incline a superior end of the platform corresponding the upper torso of a subject positioned on the platform relative to the inferior end of the platform, change the beds movement pattern, output audio and other measures the person has responded positively to in lowering snoring incidents.

The control system may also analyze the collected input data to detect a sleep apnea state. For example, analysis of input data collected by sound sensors, motion sensors, and/or other sensors suitable of measuring properties associated with detection of breathing, breathing patterns, and/or lack of breathing may correspond to a sleep apnea state. The control system may identify the sleep apnea state and then specify an output action pattern to minimize or otherwise address the sleep apnea state. For example, the control system may trigger actuators to move the platform, such as triggering irregular movements of the platform, or other patterns.

As introduced above, in some configurations, the output action specification unit 74 may generate, e.g., compute, an output action pattern, which may include one or more output actions, for the determined state. For example, the output action specification unit 74 may include a pattern generator 76 configured to generate output action patterns.

The pattern generator 76 may generate output patterns by building on and/or modifying one or more output action patterns stored in the pattern library 75 by utilizing one or more aspects of the collected input data, which may include one or more statuses. For example, in one embodiment, the processing module 70 includes a pattern generator 76 for generating output action patterns. The pattern generator 76 may generate output action patterns based at least in part on one or more values associated with measured properties, a subject status, and/or a subject state. For example, the pattern generator 76 may apply predefine rules to an output action pattern template to generate a generated output action pattern having modified output actions and/or modified parameters of output actions. In one embodiment, output patterns and/or parameters thereof may be modified based on user-controlled variables, such as personal preferences.

Output action patterns built upon or modified by the pattern generator 76 may comprise current selectable output patterns for specification or may include output pattern templates for generation of specialized output patterns. For example, the pattern generator 76 may use predefined rules that utilize one or more measured properties present in the collected input data, which may include statuses. The generated output action patterns may be specified for a current state and/or may be stored in the pattern library 75 for later specification or further modification. In one embodiment, the pattern generator 76 does not build from existing output action patterns.

Output action patterns stored in the pattern library 75 for specification may include predefined patterns or generated patterns. In some embodiments, generated patterns include output actions patterns programed for specification and execution during a learning period where the pattern generator 76 is implemented to introduce variations in the pattern. For example, the pattern generator 76 may include or interface with a machine learning engine 78 configured to analyze input data collected after initiation of a pattern, which may be a pre-programed or user generated output action pattern. In some embodiments, the machine learning engine 78 may also analyze input data collected prior to initiation of an output action pattern. In an above or another embodiment, the machine learning engine 78 may analyze statuses and/or states together with input data collected after initiation of an output action pattern and/or before initiation of an output action pattern. In one embodiment, the machine learning engine 78 analyzes historic data, e.g., input data collected with respect to previous statuses, states, specified output actions, and/or resulting impact on measured properties, statuses, and/or states during or following execution of specified output actions, to determine effectiveness of an output action pattern and its permutations to targets. In one example, this data may be derived from other users or general population. Targets may include statuses, states, and/or underlying data values corresponding to relaxation, sleep, breathing fluency, heart rate, and/or snoring reduction, for example. Using this information, the pattern generator 76 may further customize the output action pattern by suitable modification.

As introduced above, the pattern generator 76 may include or interface with the machine learning engine 78, which may be configured to utilize machine learning and/or artificial intelligence protocols to generate output action patterns, which may include parameters thereof. Machine learning engine 78 may be local to the bed device or may be remote, e.g., cloud-based or accessed via communication with one or more machine learning and/or data computational servers. Output action patterns may be generated and/or modified by the machine learning engine 78. In one embodiment, the machine learning engine 78 may modify output patterns based on user input, such as preferences, and/or based on feedback collected by sensors during past output combinations. For example, the machine learning engine 78 may determine effectiveness of a motion and/or sound, which may include one or more parameters of output motion and/or sound and/or patterns thereof, on one or more values of a subject, e.g., a value associated with a measured property, subject status, and/or subject state. This information may be used to modify output patterns and/or generate, together with the pattern generator 76, new output patterns targeted to affecting one or more properties, statuses, or states. In some embodiments, the machine learning engine 78 may modify or generate output action patterns in real time, during execution of an output action pattern. In various embodiments, different output patterns may be selected or generated based a status of a subject. For example, the output action specification unit 74 may specify an output action pattern based on how long the subject has been asleep, what sleep state they are in, or other factors, such as when the subject is to get up, whether the subject has a condition such as a fever, e.g. snoring could be caused by a cold and not part of their regular sleeping pattern, in which case a different output pattern may be specified than would be specified to address typical snoring.

The processing module 70 may include a user interface 79 for receiving inputs from a user, e.g., subject or caregiver, and/or other source. The user interface 79 may be configured to allow a user to input data related to a subject such as age, weight, gender, preferences, medical conditions, and/or target mode selection. Target mode selection, for example, may specify one or more particular modes or categories the processing module 70 is to target with respect to specified output actions. For example, a user may specify a snore mode wherein the processing module 70 specifies output actions targeting reduction in snoring or sleep apnea mode wherein the processing module 70 specifies output actions targeting minimization of sleep apnea. Target mode selection may also include a relaxation mode, sleep mode, and/or soothe mode corresponding to output action patterns or output action pattern programs, e.g., utilizing machine learning engine 78, configured to target relaxation, sleep, or soothing parameters, statuses, and/or states. In some embodiments, the processing module 70 operates in multiple modes or a general mode that targets all programmed targets based on input data, e.g., statuses and/or states. For example, the processing module 70 may target minimization of sleep apnea, snoring, relaxation, and stable sleep. The output patterns used to pursue the targets or target values may be predefined and/or generated as described above, which may include integrated machine learning.

Components of the processing unit 70 and/or user interface 79 may be located on-board and/or remotely from a bed device of the sleep system or portion thereof. For example, the user interface 79 may be an integral part of the bed device or may comprise a separate unit, such as on a mobile peripheral device, which may be connected by a wired connection, a wireless connection, or the like to the bed device. The wireless connection may be a Wi-Fi connection, Bluetooth connection, or the like. In some embodiments, the user interface 79 or portion thereof may comprise a remote user interface provided through an application run on a computing device, which may include a smart phone. The remote user interface may link directly or indirectly with the bed device via the communication module 90. Cloud-based functions may also be utilized to store user preferences and historical data for off-line processing or archiving. Off-line processing may allow more in-depth analysis that may otherwise overwhelm the processing module 70 as well as incorporate world data from multiple users and/or sources in the analysis. Such results may then be sent back to the processing module 70 to enhance or upgrade its response, functionality, or accuracy.

The user interface 79 may include controls, set-up information input, and other input data that can be sent to the processing module 70. Controls may include an on/off control, sound control, motion control, light control, or the like. Controls may be enabled or disabled.

The user interface 79 may provide cloud-based functions. Cloud-based functions may include account management, the ability to invite other account holders to manage profile, add friends, compare session data with friends, anonymously post to world data, compare session/period/epic with world data, social commenting, web view of data, and the like.

In one embodiment, the control system 50 incorporates one or more user controlled variables. User controlled variables may relate to one or more output actions and/or parameters of specific output actions or patterns thereof. For example, a user may interface with user interface 79 to select and/or define one or more output actions to be executed. In some embodiments, the output actions may be added to an output action pattern or may modify a corresponding output action of the output action pattern. In the absence of a user selecting and/or defining a user controlled variable, the control system 50 may execute an output action pattern according to the specification of the pattern. The output of the machine learning engine 78 and/or pattern generator 76 may modify or generate output action patterns based on, incorporating, and/or limited by user-controlled parameter variables, such as personal preferences. In an above or another embodiment, the machine learning engine 78 may be configured to receive user-controlled parameter variables such as sound amplitude, frequency, tone, style, cadence, transition, and/or pattern thereof; light wavelength/color, intensity, transition, and/or pattern thereof; temperature starting point, end point, rate of change, and/or temperature modification pattern; air flow speed, volume, direction, temperature, and/or pattern thereof; and/or motion frequency, amplitude, direction, transition, single axis pattern, multi-axis pattern, and/or pattern thereof. In some embodiments, the user may choose which parameters to control. When a user defines a particular parameter variable, the processing module 70 may override the parameter and/or another parameter of an executed output pattern to conform with the user defined parameter variable. In some embodiments, user specified parameters may be used to modify other output actions or their associated parameters. In one embodiment, user-controlled variables may be used by the pattern generator 76 and/or machine learning engine 78 to direct generation and/or modification of output patterns. For example, preferences or other data input by a user may be used to generate and/or modify patterns using such data together with feedback collected by sensors during past output combinations and/or current collected data and/or parameters, e.g., biological, environmental, or other parameter, status, or state.

In some embodiments, the system 10 may be configured to provide a report with respect to a subject's use of the system 10. For example, the processing module 70 may include a report generator 77. The report generator 77 may access data stored and/or collected by the system 10. In some embodiments, the user interface 79 includes a display for displaying information to a user. In one such embodiment, the report generator 77 may interface with the user interface 79 to generate a display comprising the report or a summary of the report. In another example, the report generator 77 and/or the user interface 79 may interface with the communication module 90 to transmit the report or portion thereof via email, text message, video display, voice or other suitable reporting medium. In one embodiment, the communication module 90 may distribute or make reports available, either directly or indirectly, to user applications executed on user devices, such as a laptop, smart device, television, or smart phone. User applications may be specific to the operation of the bed device or may include third-party applications. Applications may be used to input control operations, preferences, personal data, and/or provided additional input data resources, for example. Applications may be used to receive reports, analyze data, share reports with social networks or healthcare networks.

The report may be with respect to measured properties, states, statuses, and/or output actions. For example, a report may include values for measured properties such as heart rate, breathing rate, breathing frequency, blood pressure, brain waves, temperature, sleep duration, sleep states and/or sleep phase/stage durations and/or patterns. The values may be provided over time, averaged, statistically analyzed, compared to historical data, compared to general population and/or preset goals. A report may include information regarding how the subject, e.g., values of measured properties, responded to particular output actions or patterns. For example, a report may include output actions, which may also include related parameters, and how the subject responded.

A report may include differences in measured properties over time, e.g., within a session or over multiple sessions. In some embodiments, reports may identify or provide data useful for or identifying potential health conditions corresponding to values of measured properties. For example, the processing module 70 may include a health condition module configured to analyze measured properties and provide indication of potential health conditions, such as coughing or sleep apnea.

FIG. 4 illustrates an example output module 80 of the control system for a bed device. As introduced above, the sleep system may include an output module 80 configured to execute an output action pattern. As also introduced above, the processing module is configured to transmit or otherwise provide an output action pattern or corresponding control signals to the output module 80 for output of the specified output actions.

In various embodiments, the output module 80 may include a movement generation unit 82, a sound generation unit 84, a temperature modification unit 86, and/or a lighting modification unit 88. The movement generation unit 82 may be configured to execute a movement portion of an output action pattern by generating or causing generation of specified movement. The movement generation unit 82 may include or be configured to be in signal communication with one or more movement actuators 42 operable to move one or more portions of a bed device, such as a sleep platform. Movement actuators 42 may include but are not limited to motors, transmissions, airbags, motion transmitters, belts, pulleys, gears, robotics, solenoids, pneumatic pistons, and the like. The movement generation unit 82 may include or be configured for wired or wireless communication with the one or more movement actuators 42 via suitable communication ports comprising respective wired or wireless transmitters, receivers, and/or transceivers for causing a specified movement of a sleep platform or portion thereof. Movement actuators 42 may be arranged with respect to the sleep platform to cause movements of the platform that may include but are not limited to back-and-forth movements, such as linear (e.g., head-to-toe), lateral (e.g., side-to-side), vertical (up-and-down), side-to-side and/or head-to-toe tilt, and/or other movements, including combinations thereof. Movements may be along a plane with respect to the platform or along multiple planes such as up-and-down, swaying, or rocking. In a further example, such movements may comprise or include low amplitude movements, which may be provided at high frequency to result in vibratory movement. In one embodiment, movement actuators 42 may be arranged to cause the sleep platform to pivot around an axis in an arcuate motion or on an axis wherein the axis intersects the platform. In some examples, the axis may intersect a central portion, side portion, upper portion, or lower portion of the platform.

In various embodiments, movement actuators 42 may be arranged to tilt a sleep platform or portion thereof. For example, the sleep platform may be tilted to incline toward a lateral side, superior end, or inferior end. In one example, the movement generation unit 82 is configured to incline and/or decline the superior end relative to the inferior end. Thus, the movement generation unit 82 may incline and/or decline an upper body of a subject positioned on the sleep platform relative to a lower body of the subject. In this or another example, the movement generation unit 82 is configured to incline and/or decline the inferior end relative to the superior end. Thus, in some embodiments, the movement generation unit 82 may be configured incline and/or decline the lower body of the subject positioned on the sleep platform relative to the upper body of the subject. In various embodiments, the sleep platform may be movable about or relative to multiple axes. Additionally or alternatively, one or more movement actuators 42 may be positioned to move a subject, separate of the sleep platform. For example, airbags may be positioned relative to the platform for lifting/pushing the body of the subject. Motion patterns may include movement within one, two, three, four, five, or six degrees of freedom. The motion patterns may be provided with respect to the platform and/or the subject. In some examples, the sleep platform is operable to yaw, roll, pitch, surge, heave, and/or sway. Motion patterns may incorporate complex movement combination within these degrees of freedom to produce proprioceptor and/or vestibular system response in a subject. Movement actuators 42, such as actuators or motors for pushing/pulling the platform side-to-side may be used in addition to or separate from movement actuators 42 positioned to move the subject. In one example, movement actuators 42 include pistons operatively coupled to multiple locations of the platform, such as at multiple corners or other locations. In one such example, a piston is located at four or more corners of the platform. The platform may be any shape such as round, oblong, square, rectangle, or any other geometric or non-geometric shape. In one example, actuators are couple to the platform at one or more locations. In another embodiment, the platform mounts to a frame or other platform that therefore transfers movement to the platform. In various embodiments, such a frame or platform may also be considered the platform. These and other configurations may be used to create complex movements in-place, within a small footprint to advantageously create most movement patterns without requiring additional real estate. Movements may be singular, rhythmic, repetitive, dynamic, variable, or irregular. Combinational movements within one or more degrees of freedom may be designed to affect the inner ear with limited movement of the body to create a sensation of movement.

The sound generation unit 84 may be configured to execute a sound portion of an output action pattern by generating or causing generation of a specified audiotrack. The sound generation unit 84 may include or be configured to be in signal communication with one or more speakers 44 operable to emit sounds of an audiotrack specified in a sound portion of an output action pattern. The sound generation unit 84 may be configured for wired or wireless communication with the one or more speakers 44 via suitable communication ports comprising respective wired or wireless transmitters, receivers, and/or transceivers.

Speakers 44 or other sound producing devices of the sound generation unit 84 may be integrated or otherwise associated with a bed device, or sleep platform thereof. For example, one or more speakers 44 may be located on or around the bed device. In a further example, one or more speakers 44 may be positioned around a portion of the sleep platform corresponding to an intended location of a subject's head during use, such as an end of the sleep platform. In these or other embodiments, one or more speakers 44 may be located remotely of the bed device. In an above or additional embodiment, one or more speakers 44 may be integrated or associated with clothing worn by a subject or a pillow. In one example, the speaker is a directional speaker to specifically direct sound to the subject, e.g., so as to only reach the subject.

The temperature modification unit 86 may be configured to execute a temperature portion of an output action pattern by generating or causing generation of specified modification of temperature with respect to a subject, a sleep platform, or ambient air with respect to a bed device including a sleep platform. The temperature modification unit 86 may include or be configured to be in signal communication with one or more temperature modification devices 46, e.g., heaters or coolers, operable to heat, cool, and/or maintain temperature specified in an output action pattern. The temperature modification unit 86 may be configured for wired or wireless communication with the one or more temperature modification devices 46 via suitable communication ports comprising respective wired or wireless transmitters, receivers, and/or transceivers. In some embodiments, the temperature modification unit 86 may integrate with temperature control system associated with a location in which the system 10 is located. For example, the temperature modification unit 86 may communicate over a wired or wireless connection with a premises temperature control system, such as a smart thermostat, to alter temperature of the environment surrounding the bed device 20.

The one or more temperature modification devices 46 may be integrated or otherwise associated with a bed device, or sleep platform thereof. In some embodiments, one or more temperature modification devices 46 may be located on or around the bed device. For example, a sleep platform may include or be lined with heating elements and/or cooling elements operable to modify temperature of the sleep platform. In a further or another example, clothing, a sheet, or pillow may be fitted with heating and/or cooling elements. In some embodiments, a heater or air conditioner may be located proximate to the bed device and be controllable by the temperature modification unit 86 to modify ambient temperature. In some instances, the temperature portion of an output action pattern may require maintenance of a temperature by a temperature modification device 46.

In some embodiments, a temperature modification device includes a fan. The fan may be configured to produce a flow of air. The bed device or platform thereof may be configured to control a direction, speed, and/or volume of the air flow. These and other parameters/characteristics may be user controlled and/or controlled or modifiable by the output action generator, which may include the pattern generation unit 76 and/or machine learning engine 78. In various embodiments, the processing module 70 analyzes data collected by the input detection module 50, such as the environmental detection unit 66 and/or bio detection unit 68, to automatically adjust outputs in real time. For example, the output action specification unit 74 may compare target values with measured values and determine one or more output parameters to modify to achieve target values. In some embodiments, the machine learning engine 78 may be used to analyze measured values as feedback regarding environmental conditions and automatically adjust output parameters.

The lighting modification unit 88 may be configured to execute a lighting portion of an output action pattern by producing or causing production of specified lighting with respect to a subject and/or a sleep platform.

The lighting modification unit 88 may include or be configured to be in signal communication with one or more lighting modification devices 48 operable to increase, decrease, and/or modifying lighting specified in an output action pattern. The lighting modification unit 88 may be configured for wired or wireless communication with the one or more lighting modification devices 48 via suitable communication ports comprising respective wired or wireless transmitters, receivers, and/or transceivers.

The one or more lighting modification devices 48 may be integrated or otherwise associated with a bed device, or sleep platform thereof. In some embodiments, one or more lighting modification devices may be located on or around the bed device. For example, an area around a sleep platform may include or be lined with one or more light modification devices, such as lights. In some embodiments, lights may be powered on and powered off, which may include lighting patterns. Lights may include different frequencies and/or intensities. In one embodiment, the lighting modification unit 88 includes one or more actuators configured to move a light to a different location or to translate a light along a path, which may include a pattern of movements. In an above or another embodiment, the lighting modification unit 88 may include one or more light modification devices comprising an actuator operable to control light by blocking a portion of light emitted from a light source, which may include lighting modification unit 88 lights, ambient, and/or natural light. For example, the lighting modification unit 88 may employ an actuator to translate a light shield relative to a light source to modify an amount or character of the light transmitted from the light source to an area with respect to the sleep system. Thus, a light modification device 48 may include a light shield, shade, or filter that may be translated into a light path to filter all or a portion of lighting to one or more areas of a bed device, sleep platform, or a subject, or may be translated as to not obstruct transmission of light to one or more areas of the bed device, sleep platform, or the subject. In some embodiments, the lighting modification unit 88 may include or operably associate a wearable head unit, glasses, or goggles comprising one or more lights for providing light to subject and/or one or more light modification devices configured to increase, block, and/or filtering light transmitted to a subject.

As introduced above, the output module 80 may include and/or otherwise operatively couple to one or more haptic devices. Haptic devices may be operative to elicit tactile sensory perception in users. Haptic devices may include weights or other force providing devices. Haptic devices may include blankets and/or wearable devices such as straps, bands, sleeves, and/or other clothing articles that may contract, actuate, move, and/or vibrate in a touch sensory perceivable manner. For example, a haptic device comprising a shirt that includes a contractible torso portion may be worn by a user to provide a comforting contained feeling. Blankets and/or wearable devices may also include integrated massage devices that contract actuate, vibrate, and/or move to massage a user. Vibration may be generated by piezoelectric devices, eccentric rotating mass actuators, or other suitable devices. Haptic devices may also include devices not worn by users, e.g., concentrated air vortex devices and/or unworn massage devices. Such devices may be integrated or an accessory. For example, one or more massage devices may be integrated with a bed frame, mattress, pillow, or may comprise an extension thereof. Massage devices may be positioned to contact a user directly or indirectly. Massage devices may include vibration devices for generating vibrations. In some embodiments, a haptic device includes a pump or actuator configured to modify a firmness of a mattress or pillow. Haptic devices may also comprise ultrasound devices configured to direct tactile sensory perceivable ultrasound to a user. Haptic devices may be used as an aid to soothe, induce sleep, and/or induce relaxation. Haptic devices may be used to move a subject during sleep, and/or to wake a user.

It will be appreciated that one or more modules, units, and/or databases may be remote and/or distributed with respect to one or more other modules, units, and/or databases. For example, the movement generation unit, sound generation unit, temperature modification unit, and/or lighting modification unit may be local or remote with respect to the processing module or one or more units thereof. As another example, the processing module or one or more units thereof may be remote with respect to one or more units of the input detection module. Transmission of data described herein between distributed and/or remote modules, units, and/or databases may be via wired or wireless communication. For example, modules, units, and/or databases may include communication ports comprise transmitters, receivers, and/or transceivers suitable to execute such data transmissions. In one example, the input detection module, output module, or one or more units thereof may communicate with the processing module and/or one or more databases via a Wi-Fi connection. Similarly, in various embodiments, one or more units of the output module may communication with execution hardware via wired or wireless communication. For example, the movement generation unit may transmit control operations to movement generation hardware via wired or wireless communication. In this or another example, the sound generation unit may transmit audiotrack data to speakers via wired or wireless communication. In an above or another example, the temperature modification unit may transmit temperature modification data to temperature modification hardware via wired or wireless communication. In an above or another example, the lighting modification unit may transmit lighting data to lighting hardware via wired or wireless communication.

It is to be understood that an output action pattern may comprise single or combinational outputs and all specified output actions of an output action pattern need not be transmitted together as a unit. Specified output actions may be provided for execution individually or in one or more groupings to output module units, for example. Thus, the output module or a unit thereof may include a receiver or transceiver for receiving signals comprising an output action pattern or portion thereof. The signals may include data signals comprising specified output actions. For example, the processing module may include or access one or more databases and transmit a data signal comprising a specified action including instructions for executing the specified action.

In some examples, the specification may specify desired movements, sounds, temperature, and/or lighting. In some such examples, the respective databases may provide instructions with respect to the execution of the unit functions required to achieve the desired actions specified. Relevant units may obtain or be provided, e.g., in an output action pattern, current status of temperatures, sleep platform configuration/orientation, lighting, or sound, for example. In some embodiments, an output action pattern may be based on current conditions and provide instructions and/or specify suitable action.

In one example, the sleep system may include a movement database comprising instructions for producing a plurality of movements and/or patterns thereof that may be specified in an output action pattern. Such instructions may be provided in a movement portion of an output action pattern or may otherwise be directly or indirectly identified, e.g., based on specified movements or positions, such that the motion unit may execute the movement portion of the output action pattern.

In an above or another example, the control system may include a sound database comprising a plurality of audiotracks that may be specified in an output action pattern. Such audiotracks may be provided in a sound portion of an output action pattern or may otherwise be directly or indirectly identified, e.g., based on specified sounds and/or audiotracks, such that the sound generation unit may execute the sound portion of the output action pattern. In various embodiments, the sound database includes one or more audiotracks selected from white noise, variable white noise, noise cancellation, music, ambient sounds, nature sounds, variable frequency and/or amplitude sounds, and repetitive sounds.

In an above or another example, the control system may include a temperature database comprising instructions for producing a plurality of temperature modifications and/or patterns thereof that may be specified in an output action pattern. Such instructions may be provided in a temperature portion of an output action pattern or may otherwise be directly or indirectly identified, e.g., based on specified temperatures or temperature modifications, such that the temperature modification unit may execute the temperature portion of the output action pattern.

In an above or another embodiment, the control system may include a lighting database comprising instructions for producing a plurality of lighting configurations, modifications, and/or patterns thereof that may be specified in an output action pattern. Such instructions may be provided in a lighting portion of an output action pattern or may otherwise be directly or indirectly identified, e.g., based on specified lighting or lighting modifications, such that the lighting modification unit may execute the lighting portion of the output action pattern.

The present disclosure may include dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example network or system is applicable to software, firmware, and hardware implementations.

In accordance with various embodiments of the present disclosure, the processes described herein may be intended for operation as software programs running on a computer processor. Furthermore, software implementations can include, but are not limited to, distributed processing or component/object distributed processing, parallel processing, or virtual machine processing that may be constructed to implement the methods described herein.

The present disclosure describes various systems, modules, units, devices, components, and the like. Such systems, modules, units, devices, components, and/or functionalities thereof may include one or more electronic processors, e.g., microprocessors, operable to execute instructions corresponding to the functionalities described herein. Such instructions may be stored on a computer readable medium. Such systems, modules, units, devices, components, the like may include functionally related hardware, instructions, firmware, or software. For example, modules or units thereof, which may include generators or engines, may include physical or logical grouping of functionally related applications, services, resources, assets, systems, programs, databases, or the like. The systems, modules, units, which may include data storage devices such as databases and/or pattern library may include hardware storing instructions configured to execute disclosed functionalities, which may be physically located in one or more physical locations. For example, systems, modules, units, or components or functionalities thereof may be distributed across one or more networks, systems, devices, or combination thereof. It will be appreciated that the various functionalities of these features may be modular, distributed, and/or integrated over one or more physical devices. It will be appreciated that such logical partitions may not correspond to physical partitions of the data. For example, all or portions of various systems, modules, units, or devices may reside or be distributed among one or more hardware locations.

The present disclosure contemplates a machine-readable medium containing instructions so that a device connected to the communications network, another network, or a combination thereof, can send or receive voice, video or data, and to communicate over the communications network, another network, or a combination thereof, using the instructions. The instructions may further be transmitted or received over the communications network, another network, or a combination thereof, via the network interface device. The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure. The teams "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or re-organizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a lists of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" corresponds to "x and/or y" and refers to "x", "y", or both "x" and "y", whereas "either x or y" refers to exclusivity.

What is claimed is:

1. A sleep system, the system comprising:
 a bed device including a platform for supporting a subject;
 input sensors positioned to collect input data with respect to the subject, the input sensors comprising a breath sensor to measure respiration, a heart rate sensor, and a body temperature sensor;
 a control system to receive and analyze the collected input data, wherein the control system is configured to determine one or more states of the subject based on a combinational analysis of the collected input data that includes a plurality of determined statuses comprising a breathing rate and/or breathing depth status of the subject, heart rate status of the subject, and body temperature status of the subject, wherein the control system includes a machine learning engine and pattern generator configured to modify output patterns in real time based on feedback collected by the input sensors during output of the output action pattern; and
 one or more output devices operable to perform output actions specified by the control system, wherein the output devices comprise actuators to cause movements of the platform, one or more speakers positioned to direct sound toward the subject, and one or more light modification devices to modify lighting with respect to the environment surrounding the subject and/or bed device,
 wherein the control system is configured to specify an output action pattern based at least in part on the one or more states of the subject, and wherein the output action pattern comprises movement of the platform on multiple axes in combination with a sound directed toward the platform and modification of lighting,
 wherein the input sensors further comprise a sound sensor configured to collect sound data, wherein the plurality of determined statuses further include a sound status, wherein the control system is configured to determine a snoring state via a combinational analysis of the sound status, breathing rate status, and heart rate status, and wherein the output action pattern specified for the snoring state comprises inclining a superior end of the sleep platform relative to an inferior end of the platform,
 wherein, the output pattern specified for a determined snoring state is different than the output pattern specified for a determination of both a snoring state and a cold state.

2. The sleep system of claim 1, wherein the plurality of determined statuses includes statuses related to movement of the subject over time, acceleration of the subject, gross movement of the subject and/or proximate environment, subject body orientation, changes in body orientation over time, sound frequency and/or amplitude with respect to the environment surrounding the subject, ambient light intensity/amplitude and/or wavelength/frequency, heart rhythm, breathing rhythm, respiration quality, temperature of platform, blood pressure, weight of subject, or combination thereof, wherein the input sensors further comprise a light sensor, and wherein the input data analyzed by the control system further comprises a determined light status including ambient light intensity and wavelength.

3. The sleep system of claim 1, wherein the output action pattern comprises movement of the platform in six degrees of freedom to produce proprioceptor and/or vestibular system response in the subject, wherein the sound directed to the subject comprises variable white noise, and wherein the movement comprises sliding the platform back-and-forth or pivoting the platform on an axis.

4. The sleep system of claim 3, wherein the input sensors further comprise a temperature sensor configured to collect temperature data with respect to the temperature of the platform or surrounding environment, and wherein the output action pattern further includes modification of the temperature of the platform or surrounding environment.

5. The sleep system of claim 1, wherein the state of the subject includes an apnea event, and wherein the output action pattern specifies irregular movements of the sleep platform in response to the apnea event.

6. The system of claim 1, wherein the input sensors further comprise an electroencephalography (EEG) sensor, and wherein the combinational analysis of the collected input data further includes a determined brain biofeedback status of the subject.

7. The system of claim 6, wherein the brain biofeedback status comprises a consciousness status determined from comparison of brainwaves or rhythm thereof of alpha brainwaves, delta brainwaves, or both and beta brainwaves, gamma brainwaves, theta brainwaves, or combination thereof.

8. The system of claim 1, wherein the machine learning engine and pattern generator are configured to modify output patterns based on feedback collected by the input sensors during output of previous output patterns.

9. The system of claim 8, wherein the combinational analysis to determine at least one of the states includes a duration of two or more of the plurality of determined statuses.

10. The system of claim 9, wherein the output action pattern is directed to eliciting a target outcome with respect to the subject.

11. The system of claim 10, wherein the targeted outcome comprises one more of stimulation of relaxation, initiation of sleep, continuation of sleep, a duration of sleep, depth of sleep, cessation of snoring, or breathing fluency.

12. A method of controlling a bed device having a movable platform for supporting a subject, the method comprising:
collecting input data from one or more input sensors positioned to measure parameters with respect to the subject, wherein the input sensors comprise a breath sensor to measure respiration, a heart rate sensor, a body temperature sensor, and a sound sensor configured to collect sound data;
analyzing the collected input data to determine a plurality of statuses, wherein the statuses comprise a breathing rate and/or breathing depth status of the subject, a heart rate status of the subject, a body temperature status of the subject, and a sound status;
converting the determined statuses to one or more states of the subject via a combinational analysis of the determined statuses, wherein the converting comprises converting the determined statuses to a snoring state via a combinational analysis of the sound status, breathing rate status, and heart rate status;
identifying an output action pattern corresponding to the state of the subject, wherein the output action pattern comprises movement of the platform in combination with a sound directed toward the subject and modification of lighting, wherein the output action pattern corresponding to the snoring state comprises inclining a superior end of the sleep platform relative to an inferior end of the platform, wherein, the output action pattern corresponding to the snoring state is different than the output action pattern corresponding to a conversion of the determined statuses to both a snoring state and a cold state;
executing the output action pattern utilizing one or more output devices comprising an actuator configured to cause movement of the platform, a speaker directed toward the platform, and a light modification device; and
modifying the output pattern in real time based on feedback collected by the input sensors during output of the output action pattern.

13. The method of claim 12, wherein the statuses of the subject further include heart rhythm, breathing rate, breathing depth, breathing rhythm, respiration quality, blood pressure, weight of subject, or combination thereof.

14. The method of claim 12, wherein the input sensors further comprise an electroencephalography (EEG) sensor, and wherein the combinational analysis of the collected input data further includes a determined brain biofeedback status of the subject.

15. The method of claim 14, wherein the brain biofeedback status comprises a consciousness status determined from comparison of brainwaves or rhythm thereof of alpha brainwaves, delta brainwaves, or both and beta brainwaves, gamma brainwaves, theta brainwaves, or combination thereof.

16. The method of claim 12, further comprising modifying the output pattern based on feedback collected by the input sensors during output of a previous output pattern.

* * * * *